(12) United States Patent
Shi

(10) Patent No.: US 9,844,327 B2
(45) Date of Patent: Dec. 19, 2017

(54) SAFETY LANCING DEVICE

(71) Applicant: STERILANCE MEDICAL (SUZHOU) INC., Suzhou, Jiangsu (CN)

(72) Inventor: Guoping Shi, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 327 days.

(21) Appl. No.: 14/774,934

(22) PCT Filed: Mar. 17, 2014

(86) PCT No.: PCT/CN2014/073543
§ 371 (c)(1),
(2) Date: Sep. 11, 2015

(87) PCT Pub. No.: WO2014/146560
PCT Pub. Date: Sep. 25, 2014

(65) Prior Publication Data
US 2016/0022177 A1    Jan. 28, 2016

(30) Foreign Application Priority Data

Mar. 18, 2013  (CN) .......................... 2013 1 0086237

(51) Int. Cl.
*A61B 5/151*    (2006.01)
*A61B 5/15*    (2006.01)

(52) U.S. Cl.
CPC .......... *A61B 5/1411* (2013.01); *A61B 5/1519* (2013.01); *A61B 5/150022* (2013.01); *A61B 5/15113* (2013.01); *A61B 5/15117* (2013.01); *A61B 5/150183* (2013.01); *A61B 5/15194* (2013.01); *A61B 5/150412* (2013.01); *A61B 5/150503* (2013.01)

(58) Field of Classification Search
CPC ............ A61B 5/1411; A61B 5/150022; A61B 5/150412; A61B 5/15113; A61B 5/15117; A61B 5/15194; A61B 5/150183; A61B 5/150503; A61B 5/1519
See application file for complete search history.

(56) References Cited

U.S. PATENT DOCUMENTS

| | | | |
|---|---|---|---|
| 6,197,040 B1* | 3/2001 | LeVaughn | A61B 5/150022 600/583 |
| 2010/0094324 A1* | 4/2010 | Huang | A61B 5/150022 606/182 |
| 2011/0313439 A1* | 12/2011 | Ishikura | A61B 5/1411 606/182 |

* cited by examiner

Primary Examiner — Katherine Rodjom
(74) Attorney, Agent, or Firm — Oliff PLC

(57) ABSTRACT

A kind of safety lancing device has a front cap and lancet holder with feature: the front cap and lancet holder are connected in insert-plug type, and the front cap is equipped with connecting block at connection end and the lancet holder is equipped with slot at connection end. And the slot includes slideable slot and deadlock slot. The slideable slot is located in front of deadlock slot. The latch is set at the flexible arm end of ejection pin and the latch is equipped with bayonet at the front end and equipped with latch hook at rear end; the width of slideable slot and deadlock slot is larger than that of latch; the slideable slot is equipped with a blocking shoulder at rear end and the deadlock slot is equipped with latching shoulder at front end.

6 Claims, 17 Drawing Sheets

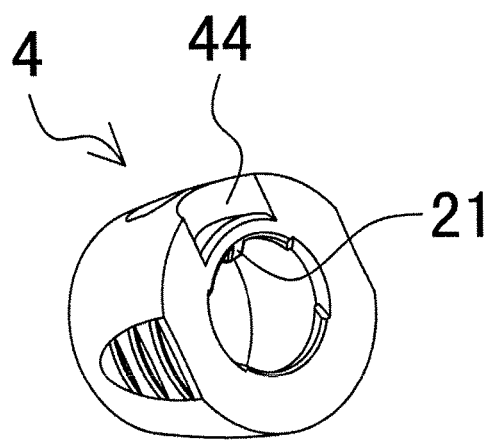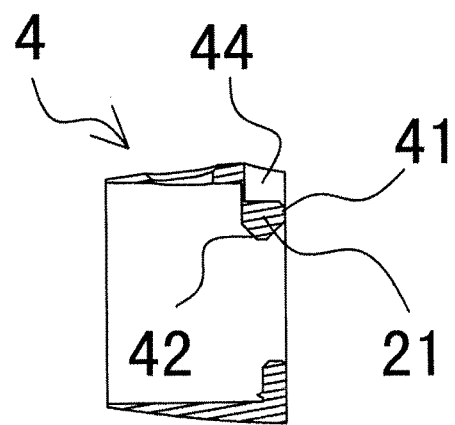
FIG. 4          FIG. 5
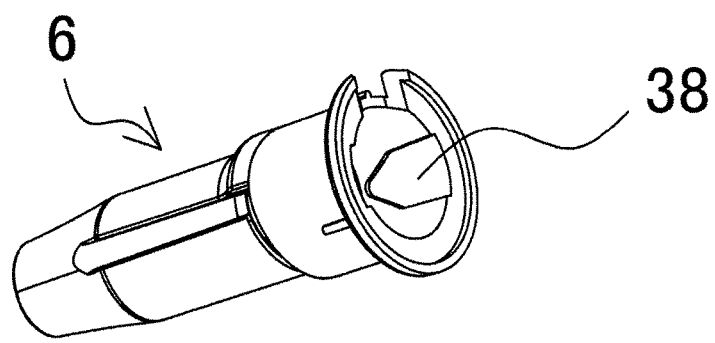
FIG. 6

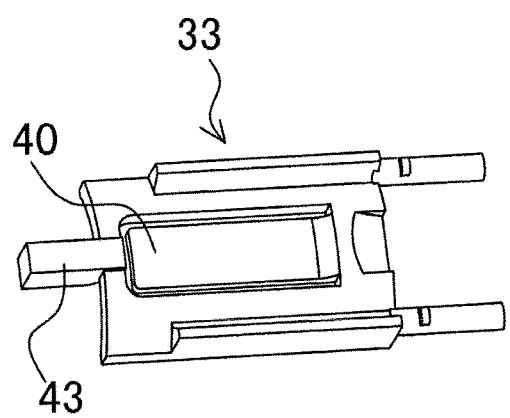
FIG. 13
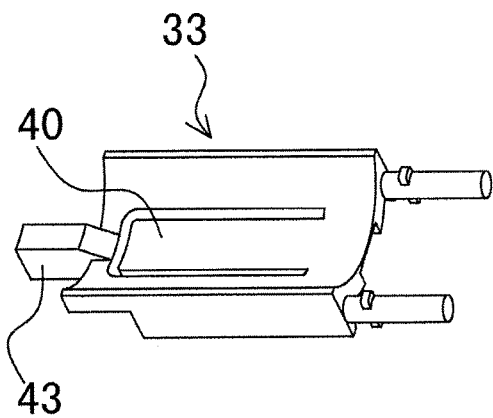
FIG. 14
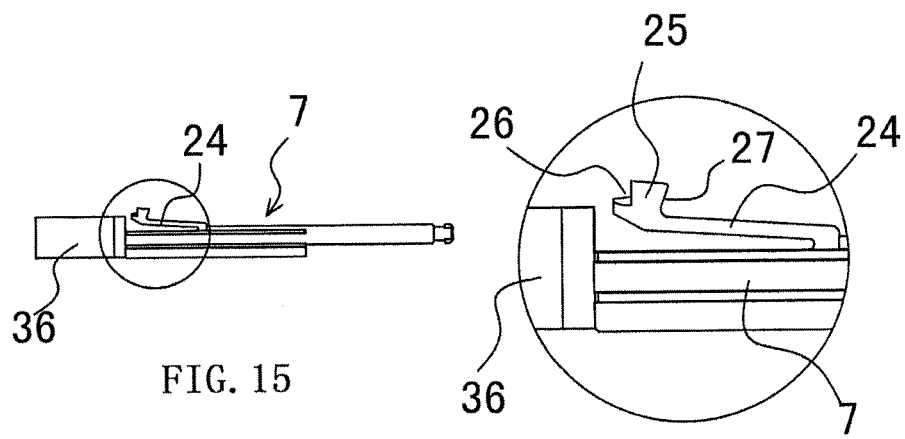
FIG. 15
FIG. 16

SAFETY LANCING DEVICE

TECHNICAL FIELD

The present invention relates to the medical lancing device, especially relates to a kind of safety lancing device used with the disposable lancet.

BACKGROUND OF INVENTION

The lancing device is a kind of ejecting device and it's usually used with the disposable lancet wherein the lancing device could be used repeatedly, but the lancet is disposable in order to avoid the cross infection. The lancing device has been developed for more than a decade, and the lancing device has been improved many times and it's becoming mature, but the safety and convenience during use of lancing device are always the concerns of the technical person in this field.

On Jan. 9, 2013, Chinese patent CN102379705B published and authorized an invention patent titled A Kind of Safety Lancing Device. This patent related the insert-plug connection of front cap and lancet holder with the safety of operating the lancing device and cleverly used the insert-plug connection of front cap and lancet holder to solve the potential safety problem during the operation process. But in the practical use, it's found that during the insertion of front cap and lancet holder, it's required to align the push pin on the connection end of front cap with the transition slot on the connection end of lancet holder for insertion, which has higher requirement on operation and causes inconvenience for operation. Especially for the aged users with poor eyesight and shaking hands, it's very difficult for them to align the front cap with lancet holder for insertion. Therefore, the present invention is to improve the existing technology to lower the requirement of alignment of front cap and lancet holder and improve the operation convenience.

DISCLOSURE OF THE INVENTION

The present invention provides a kind of improved safety lancing device, which is to ensure the operation safety and lower the requirement of alignment of front cap and lancet holder and improve the operation convenience to solve the operation inconvenience problem of existing safety lancing device in the background of invention.

In order to achieve the above-mentioned purpose, the present invention applies the technical solution: a kind of improved safety lancing device consists of a front cap and a lancet holder. The front cap is internally equipped with ejecting cavity in axial direction. The needle hole is set at front end of ejecting cavity and the lancet holder is equipped with ejection pin and ejecting spring. The ejection pin is set with a socket to plug the lancet at the head end and the lancet holder is set with release button at the side and set with tail handle at the tail end. The rear end of front cap is deemed as first connection end and the lancet holder is set with second connection end corresponding to first connection end at the front end. And first connection end and second connection end are connected in insert-plug type wherein:

The inner wall of ejecting cavity of above-mentioned first connection end is set with a connecting block, which is set with a pushing face facing the direction of second connection end and is set with a bulge facing the direction of cross section of ejecting cavity. The shape of bulge is conic, trapezoid or arc on the axial section of front cap;

The second connection end is set with a section of tubular body along the axial direction of lancet holder corresponding to the mentioned connecting block and the tubular body is set with a slot on the tube wall along axial direction facing the connecting block. And the slot intersects the tube wall in the radial direction of lancet holder;

A flexible arm extends out from the side of ejection pin and the flexible arm is set with a latch at the cantilever beam end. The latch is set with a bayonet at the front end and a latch hook on the rear end;

The mentioned slot has a section of slideable slot and a section of deadlock slot in the axial direction of lancet holder. The slideable slot is located in front of deadlock slot. In radial direction of lancet holder, the width of slideable slot and deadlock slot is larger than that of latch; the front end of slideable slot 28 is open ended and the slideable slot forms a blocking shoulder at rear end and the deadlock slot forms a latching shoulder at front end; the release button is located above the deadlock slot and a locking block is set between the release button and deadlock slot. The locking block is slidably connected to tubular body and the sliding direction is parallel to axial direction of tubular body. A locking spring is set between locking block and tubular body and the locking spring acts on the sliding direction of locking block, which is set with a spring tongue or a window. The spring tongue is an elastic piece with cantilever beam and it's located between release button and deadlock slot. And the cantilever beam of spring tongue is hanged relatively to locking block;

When the front cap and lancet holder are separated, the locking spring forces the locking block to move to the front end of sliding path and the cantilever beam or window of spring tongue travels across the latching shoulder to be located above the latching shoulder to make release button in locking state; when the ejecting spring is in free state, the latch is located in slideable slot, and when the lancet is inserted into the socket under such state, the inserting forces the latch hook of latch to work with blocking shoulder to prevent the latch from sliding from slideable slot to deadlock slot;

When the front cap is inserted into lancet holder for connection, the connecting block is inserted into slideable slot. During the insertion process, the bulge on the connecting block forces the latch hook of latch to avoid the blocking shoulder by pressing the latch to push the flexible arm to be bent toward the inner side of lancet holder and the pushing face of connecting block pushes the locking block to move backwards driving the cantilever beam or window of spring tongue to avoid the latching shoulder and making release button enter the unlocking state. Under such state, when the tail handle is pulled backward, the ejection pin drives the latch to travel across the slideable slot to enter the deadlock slot through the flexible arm, and when the tail handle returns to original position, the bayonet at front end of latch is locked in the latching shoulder to make ejection pin enter the locking state before firing under the elastic force of ejecting spring and flexible arm; when the release button is pressed, the release button acts on the latch through the cantilever beam or window of spring tongue to make bayonet slide downward along the latching shoulder until it's unhooked to enter the firing state;

Under the locking state of ejection pin before firing, when the front cap is pulled out of lancet holder, the connecting block is pulled out of slideable slot at the same time, and the locking spring forces the locking block to move forward to the front end and the cantilever beam or window of spring tongue travels across the latching shoulder to be located up front of latching shoulder to make release button enter locking state. Under such state, the pressing of release button is ineffective.

The above described technical solution is explained as follows:

1. In above described technical solution, the "front" in mentioned "front end", "foreside" and "forward" refers to direction of tip of lancing device or ejection direction of lancet. The "rear" in mentioned "rear end", "rearward" and "backward" refers to the tail of lancing device or the opposite direction of ejection of lancet.

2. In above described technical solution, the "axial direction of lancet holder" refers to axis direction of lancet holder, i.e. the direction between tip and tail of lancing device or anteroposterior direction. The mentioned "radial direction of lancet holder" refers to the diametral direction of lancet holder, i.e. horizontal direction of lancing device.

3. In above described technical solution, "up" and "down" in "up", "upward", "down" and "downward" is described with reference to the direction shown in FIG. 2 of present invention. As the lancing device of present invention could rotate around the axis, "up" and "down" are relative, so it's necessary to refer to the direction shown in FIG. 2.

4. In above described technical solution, the locking block is set with a sliding block at front end. When the front cap is inserted into the lancet holder for connection, the pushing face of connecting block contacts the front face of sliding block to push the locking block backward. A section of transition slot is set between slideable slot and deadlock slot to make the slot comprise of a section of slideable slot, a section of transition slot and a section of deadlock slot in the axial direction of lancet holder. The width of transition slot is less than the width of latch. Under the loading state, the sliding block at front end of locking block is in the transition slot and slides along with transition slot.

5. In above described technical solution, a hollow guiding slot is set on the inner wall of ejecting cavity of first connection end of front cap and a raised guiding track is set on the outer wall of tubular body of second connection end of lancet holder corresponding to guiding slot. When the front cap is inserted into lancet holder for connection, the guiding track and guiding slot are connected. On the matching surface of insert-plug connection of first connection end and second connection end, one side is set with a recess and the other side is set with a convex. When the front cap is inserted into lancet holder for connection, the recess and convex match together.

6. In above described technical solution, the tail of lancet holder is equipped with transparent ring and the tail of ejection pin is equipped with indication sleeve. When the ejection pin is in the locking state before firing, the indication sleeve is located in the transparent ring of lancet holder in axial direction.

In order to solve the safety problem during operation of lancing device, the present invention relates the insert-plug connection of front cap and lancet holder with safety of operating lancing device and uses the relationship among connecting block of front cap, slots of lancet holder, locking block and the latch on the flexible arm of ejection pin to solve the potential safety danger during operation of lancing device. The safety of present invention is ensured by two aspects: Firstly, during the insertion of lancet into the lancing device of present invention, as the latch is located in the slideable slot, the insertion force drives the latch to move backward, and the latch hook at rear of latch is blocked by the blocking shoulder to stop moving backward. Therefore, the insertion force will not make the firing mechanism enter the locking state in advance before firing. Only when the front cap is inserted into the lancet holder, the tail handle could be pulled to make the firing mechanism enter the locking state before firing, so it solves the potential safety danger during installation of lancet to the lancing device. Secondly, under the locking state before firing, when the front cap is pulled out of lancet holder, the connecting block is pulled out of slideable slot at the same time, and the locking spring forces the locking block to move forward to the front end and the front end of spring tongue is located above the latching shoulder to make release button enter locking state. Under such state, the pressing of release button is ineffective, which solve the potential safety danger when the front cap is opened.

The present invention improves the push pin mentioned in the background of invention to the connecting block and also adds the design of locking block, which greatly lowers the requirement of alignment of front cap and lancet holder and improves the operation convenience to solve the operation inconvenience problem of existing safety lancing device in the background of invention.

BRIEF DESCRIPTION OF THE DRAWINGS

FIG. 4 is a perspective view of adjustment ring in front cap of improved safety lancing device of present invention;

FIG. 5 is a cross sectional view of adjustment ring in front cap of improved safety lancing device of present invention;

FIG. 6 is a perspective view of adjustment core in front cap of improved safety lancing device of present invention;

FIG. 13 is a perspective view of movable locking block in lancet holder of improved safety lancing device of present invention (I);

FIG. 14 is a perspective view of movable locking block in lancet holder of improved safety lancing device of present invention (II);

FIG. 15 is a front view of ejection pin in lancet holder of improved safety lancing device of present invention;

FIG. 16 is a local enlarged view of FIG. 15;

In above figures: 1. front cap; 2. lancet holder; 3. adjustment cap; 4. adjustment ring; 5. elastic ring; 6. adjustment core; 7. ejection pin; 8. ejecting spring; 9. medium sleeve; 10. release button; 11. external sleeve; 12. unloading pin; 13. internal sleeve; 14. reset spring; 15. indication sleeve; 16. tail handle; 17. transparent ring; 18. tail cap; 19. first connection end; 20. second connection end; 21. connecting block; 22. tubular body; 23. slot; 24. flexible arm; 25. latch; 26. bayonet; 27. latch hook; 28. slideable slot; 29. transition slot; 30. deadlock slot; 31. blocking shoulder; 32. latching shoulder; 33. locking block; 34. locking spring; 35. lancet; 36. socket; 37. needle hole; 38. guiding slot; 39. guiding track; 40. spring tongue; 41. pushing face; 42. bulge; 43. sliding block; 44. recess; 45. convex.

SPECIFIC EMBODIMENT

With reference to the accompanying drawings and embodiment, the present invention will be described in detail.

Embodiment: A Kind of Improved Safety Lancing Device

Figure 1:
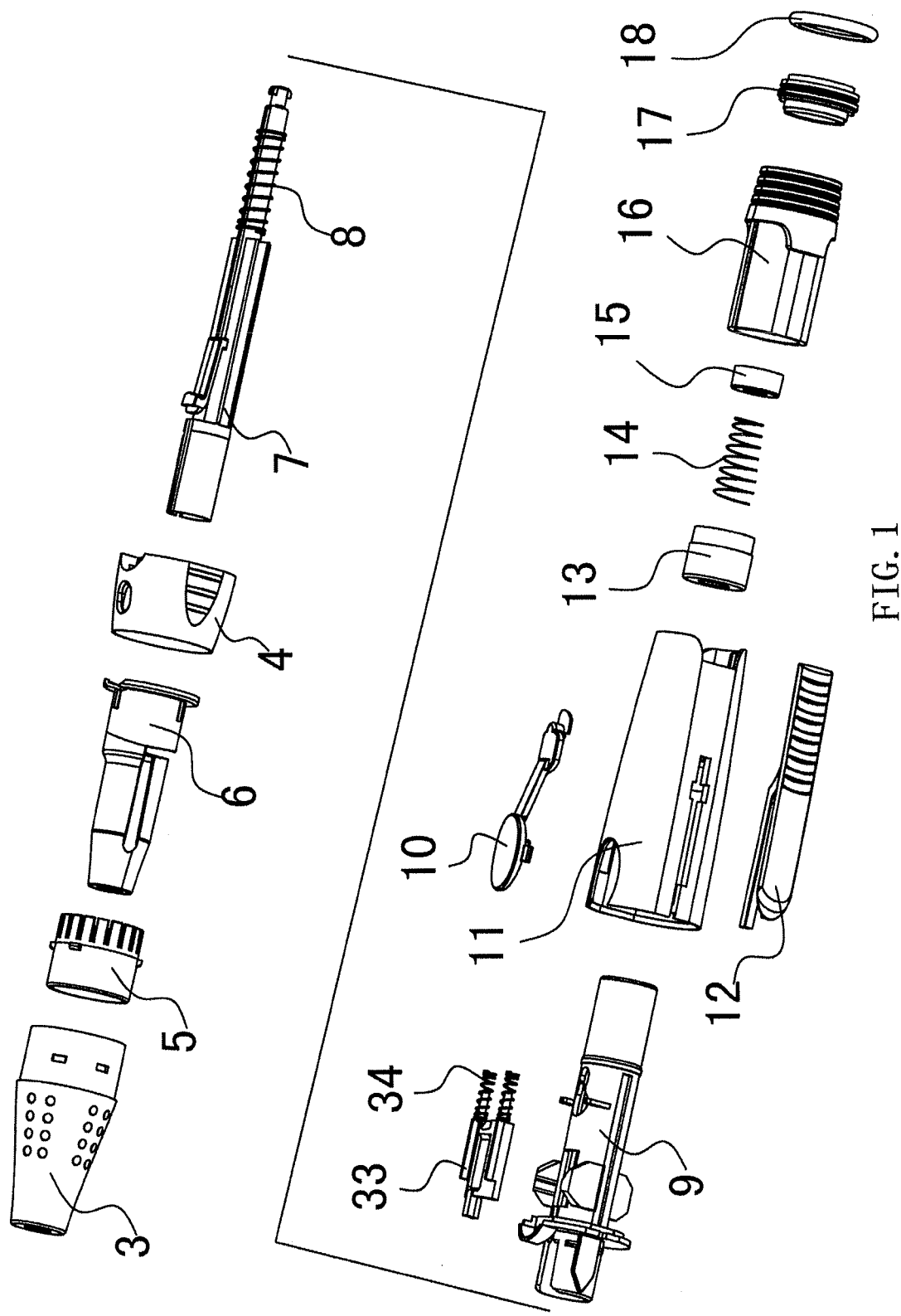
FIG. 1 is an exploded view of embodiment of improved safety lancing device of present invention.
Figure 2:
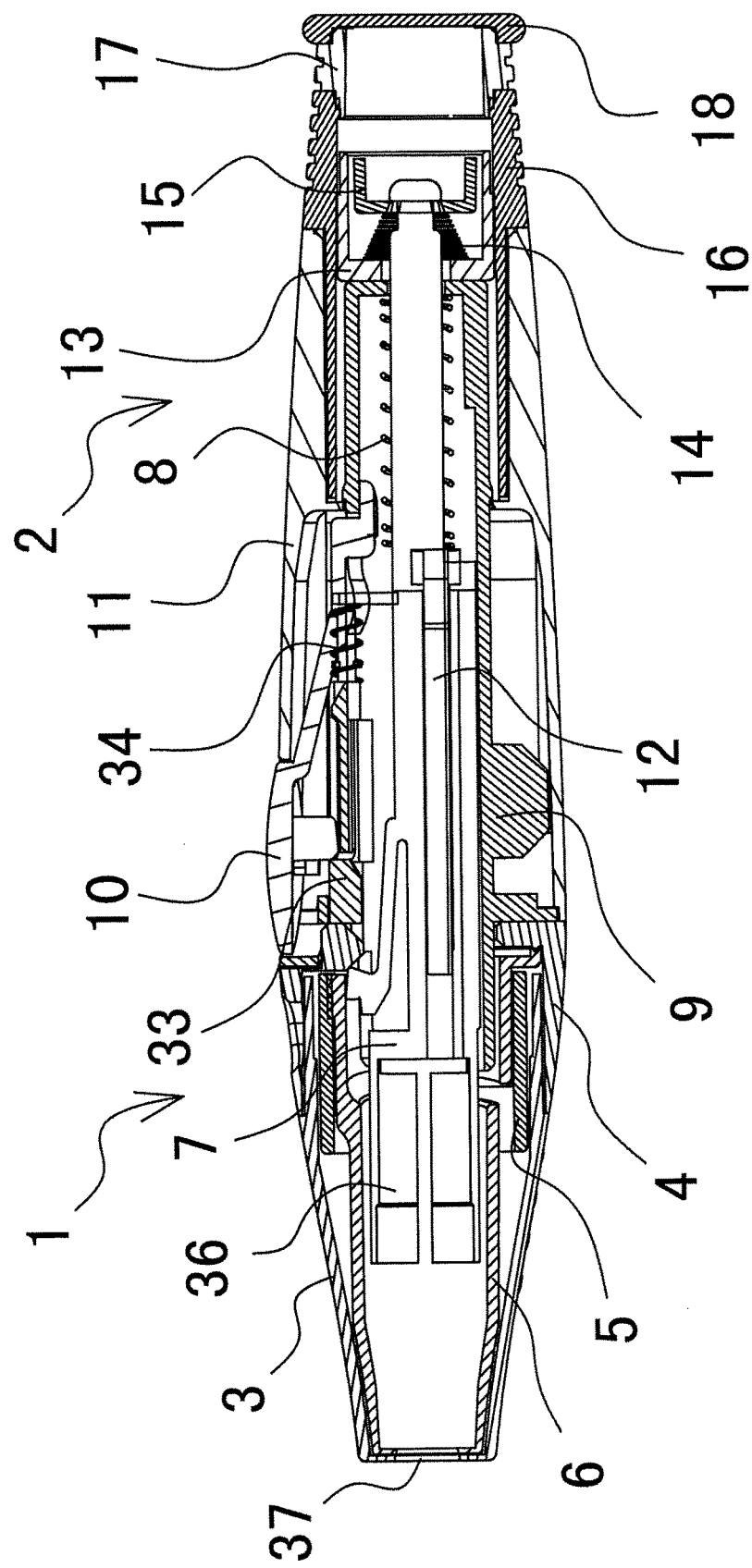
FIG. 2 is a cross sectional view of embodiment of improved safety lancing device of present invention.

As shown in FIG. 1~2, the improved safety lancing device consists of front cap 1 and lancet holder 2 wherein the front cap 1 consists of: adjustment cap 3, adjustment ring 4, elastic ring 5 and adjustment core 6. Refer to FIG. 1 for perspective view of four components and refer to FIG. 2 for assembly drawing. In the front cap 1, the adjustment core 6 is set with a ejecting cavity in axial direction and the ejecting cavity is set with a needle hole 37 at the front end. The adjustment core 6 is fixed with a adjustment ring 4 by welding or seizing and the adjustment cap 3 and elastic ring 5 are fixed by seizing and the adjustment cap 3 is installed in the head of adjustment core 6. When the adjustment cap 3 is rotated, adjustment cap 3 moves axially relative to adjustment core 6 to achieve the function of adjusting the puncture depth. The lancet holder 2 consists of following 14 components: ejection pin 7, ejecting spring 8, medium sleeve 9, locking block 33, locking spring 34 (two), release button 10, external sleeve 11, unloading pin 12, internal sleeve 13, reset spring 14, indication sleeve 15, tail handle 16, transparent ring 17 and tail cap 18. Refer to FIG. 1 for perspective view of 14 components and refer to FIG. 2 for assembly drawing. In the lancet holder 2, the medium sleeve 9 is installed inside the external sleeve 11, and the front end of medium sleeve 9 extends out of the front end of external sleeve 11 and the medium sleeve 9 and external sleeve 11 are permanently connected after they're fitted tightly. The tail of release button 10 is located in the location hole of medium sleeve 9 and the head of release button 10 is located in the button hole at the side of external sleeve 11. The tail handle 16 is installed at the tail of external sleeve 11 and slideably connected in relative to external sleeve 11. The internal sleeve 13 is fixedly connected in tail handle 16 and the tail handle 16 is fixedly connected with transparent ring 17 and tail cap 18 at the tail. The unloading pin 12 is slideably installed on the external sleeve 11 and the pushing pin of unloading pin 12 extends into the ejection pin 7. The ejection pin 7 is intalled in the medium sleeve 9 and slideably connected in axial direction in relative to medium sleeve 9 and the ejection pin 7 is set with the socket 36 to install the lancet 35 and the it's installed with ejecting spring 8 at the tail and the ejecting spring 8 acts in the middle of ejection pin 7 and medium sleeve 9 in the axial direction. The reset spring 14 acts in the middle of internal sleeve 13 and indication sleeve 15 in axial direction.

Figure 3:
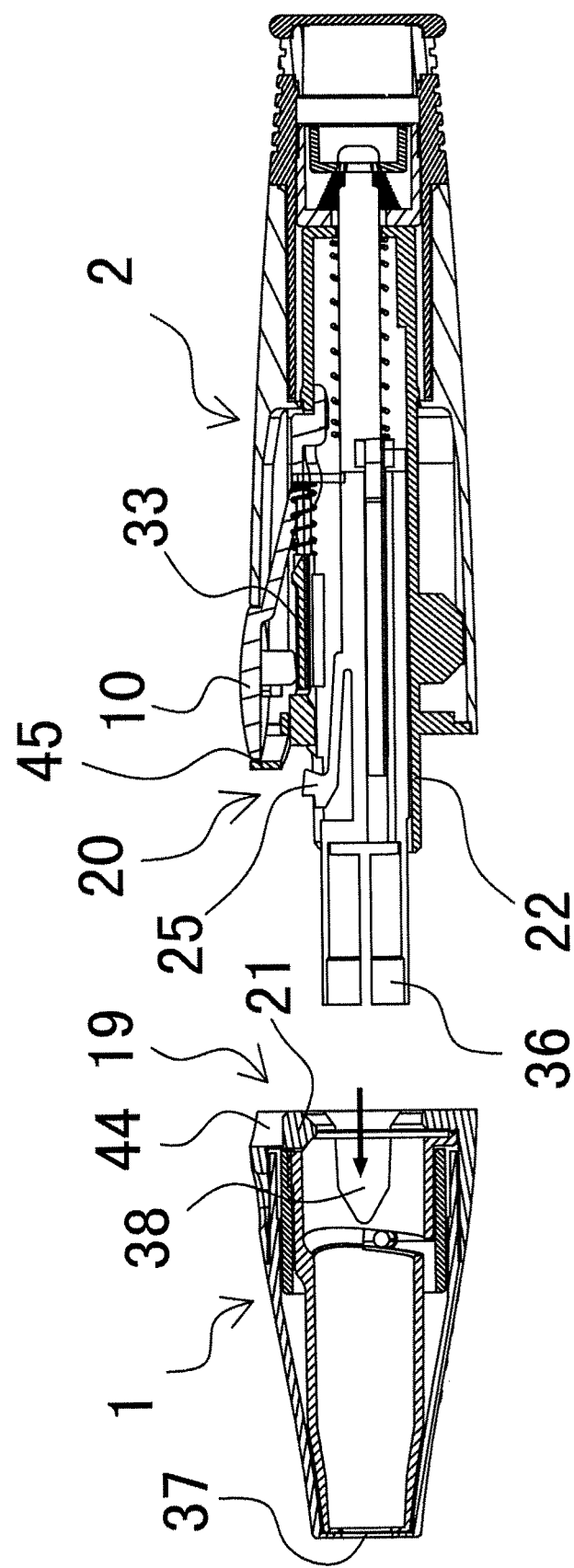
FIG. 3 is a state view of pulling out the front cap of improved safety lancing device of present invention.
Figure 7:
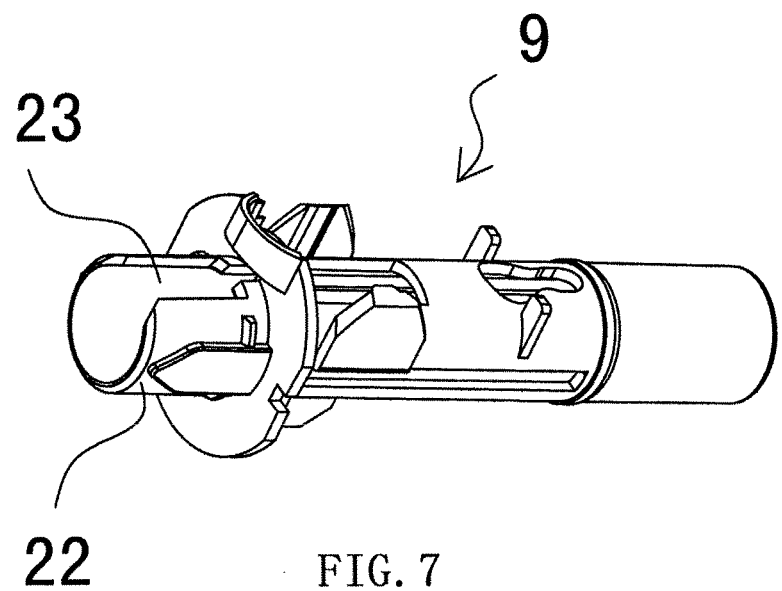
FIG. 7 is a perspective view of medium sleeve in lancet holder of improved safety lancing device of present invention (I)

As shown in FIG. 3, the rear end of front cap 1 is deemed as first connection end 19 and the lancet holder 2 is set with second connection end 20 corresponding to first connection end 19 at the front end. And first connection end 19 and second connection end 20 are connected in insert-plug type. A hollow guiding slot 38 (shown in FIGS. 3 and 6) is set on the inner wall of ejecting cavity of first connection end 19 and a raised guiding track 39 (shown in FIGS. 8, 10 and 12) is set on the outer wall of tubular body 22 of second connection end 20 of lancet holder 2 corresponding to guiding slot 38. When the front cap 1 is inserted into lancet holder 2 for connection, the guiding track 39 and guiding slot 38 are connected. Additionally, on the matching surface of insert-plug connection of first connection end 19 and second connection end 20, the first connection end 19 is set with a recess 44 (shown in FIGS. 3, 4 and 5) and the second connection end 20 is set with a convex 45 (shown in FIGS. 3, 8, 10 and 12). When the front cap 1 is inserted into lancet holder 2 for connection, the recess 44 and convex 45 match together. In order to solve the safety problem during operation of lancing device, the inner wall of ejecting cavity of above-mentioned first connection end 19 is set with a connecting block 21 (shown in FIG. 3).

As shown in FIGS. 4 and 5, the mentioned connecting block 21 is actually set in the inner hole end of adjustment ring 4 (shown in FIG. 5), and the connecting block 21 is set with a pushing face 41 facing the direction of second connection end 20 and is set with a convex 42 facing the direction of cross section of ejecting cavity. The shape of convex 42 is conic, trapezoid or arc on the axial section of front cap 1 (in FIG. 5, it's trapezoid).

Figure 8:
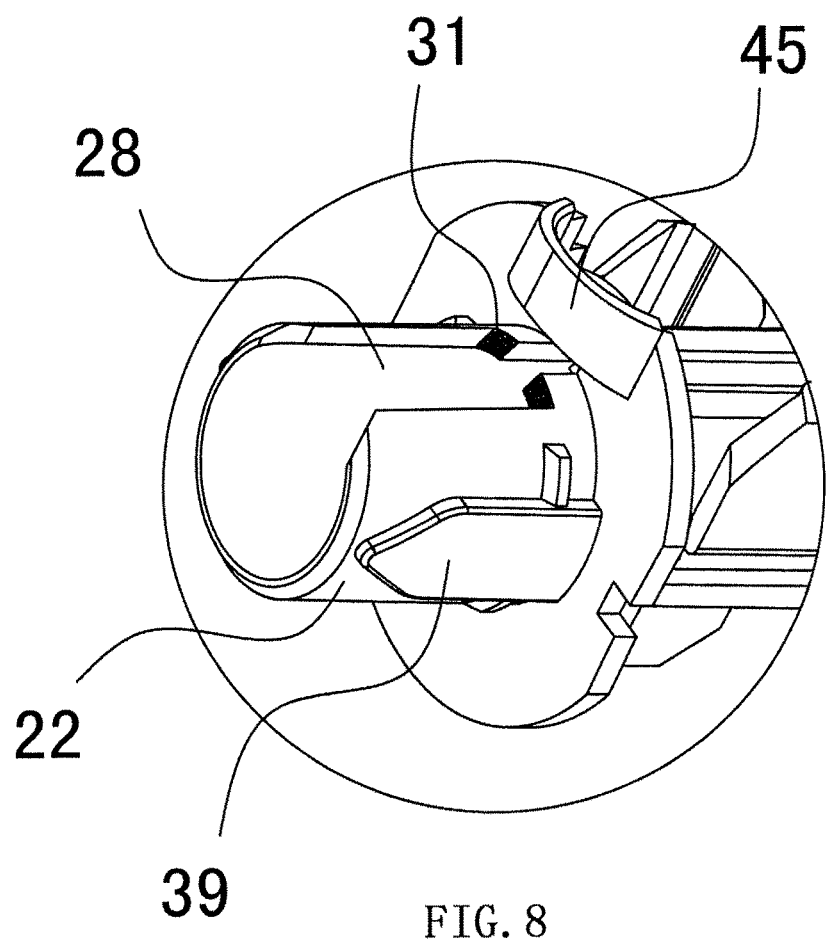
FIG. 8 is a local enlarged view of FIG. 7.
Figure 9:
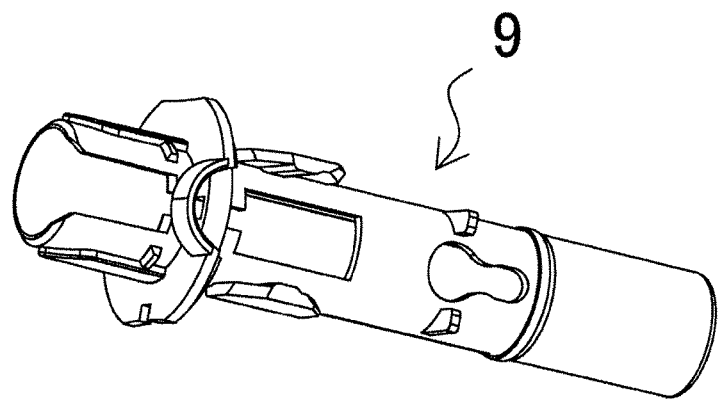
FIG. 9 is a perspective view of medium sleeve in lancet holder of improved safety lancing device of present invention (II)
Figure 10:
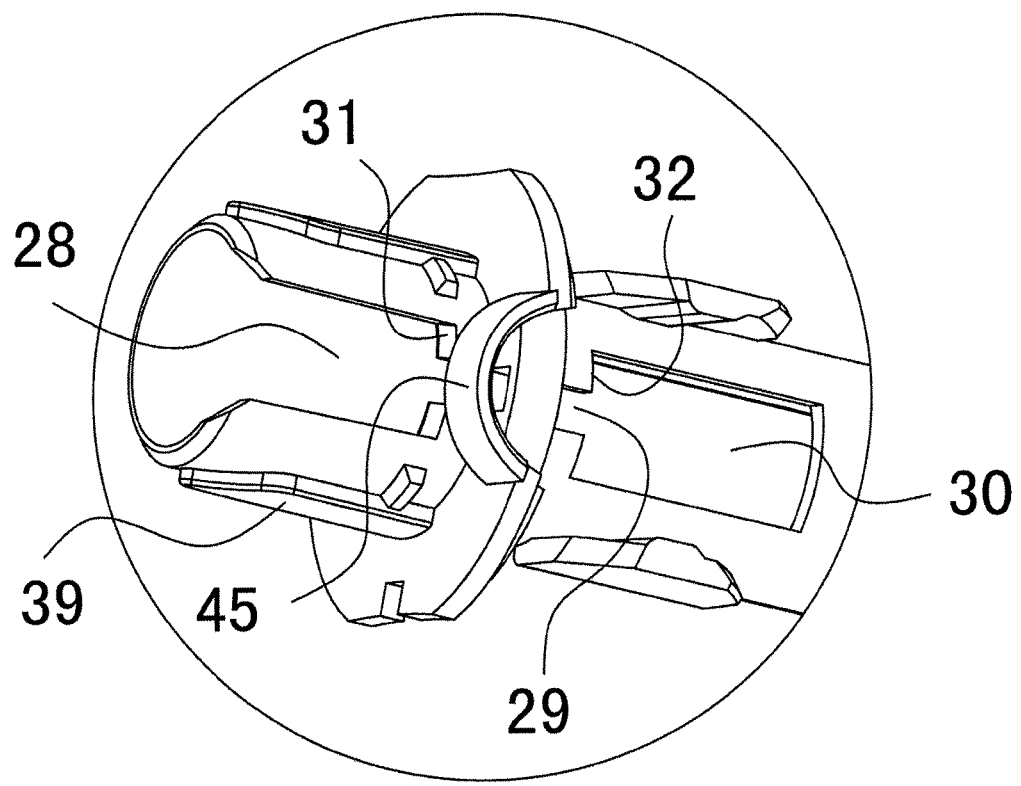
FIG. 10 is a local enlarged view of FIG. 9.
Figure 11:
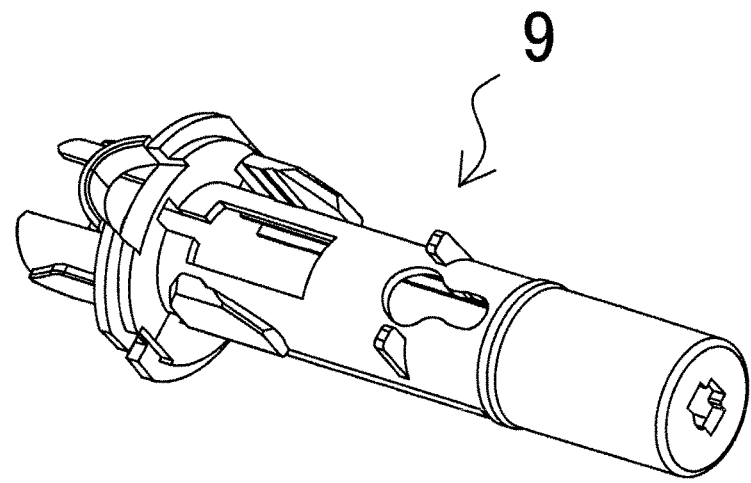
FIG. 11 is a perspective view of medium sleeve in lancet holder of improved safety lancing device of present invention (III)
Figure 12:
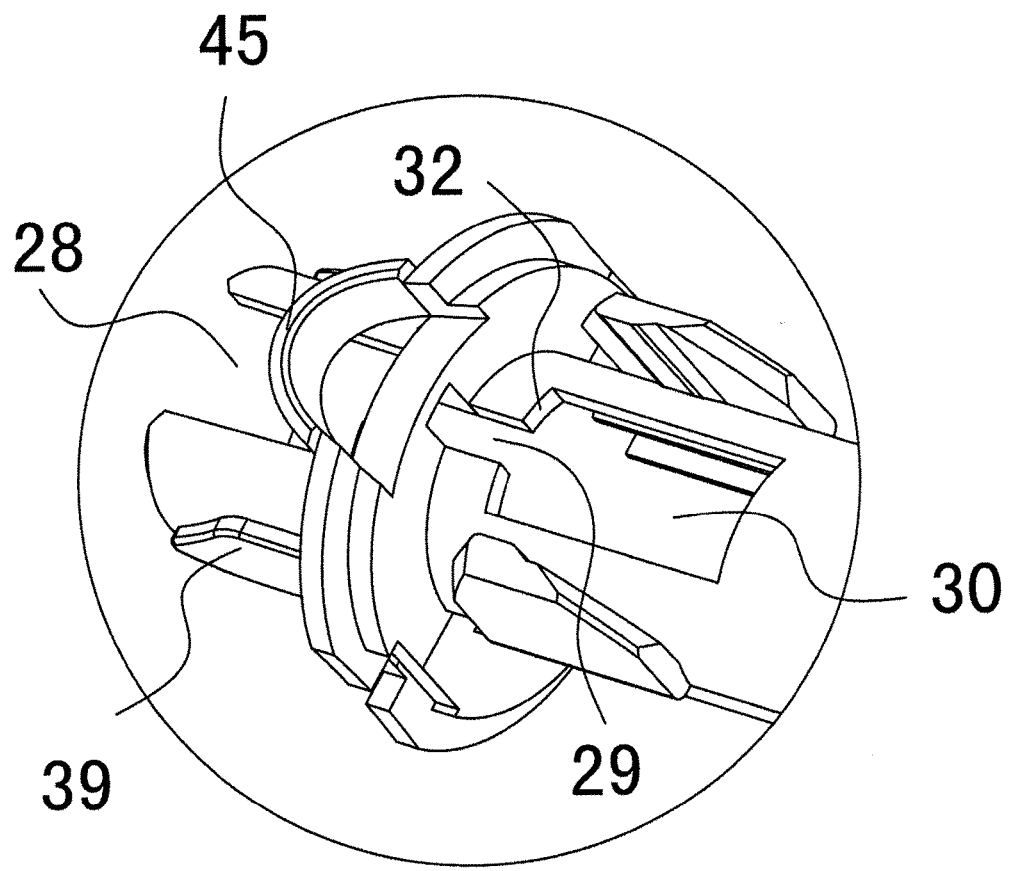
FIG. 12 is a local enlarged view of FIG. 11.

As shown in FIG. 6, the guiding slot 38 located in the first connection end 19 is set in the inner hole end of adjustment core 6 and it's used to be connected with the guiding track 39 on the second connection end 20 (shown in FIGS. 8, 10 and 12).

As shown in FIG. 7~12, the second connection end 20 is set with a section of tubular body 22 along the axial direction of lancet holder 2 corresponding to the mentioned connecting block 21 and the tubular body 22 is set with a slot 23 on the tube wall along axial direction facing the connecting block 21. And the slot 23 intersects the tube wall in the radial direction of lancet holder 2.

The above-mentioned slot 23 comprises of a section of slideable slot 28, a section of transition slot 29 and a section of deadlock slot 30 in the axial direction of lancet holder. The slideable slot 28 is located in front of deadlock slot 30. In the radial direction of lancet holder 2, the width of slideable slot 28 and deadlock slot 30 is larger than width of latch 25 and the width of transition slot 29 is less than width of latch 25. The front end of slideable slot 28 is open ended and the slideable slot 28 forms the blocking shoulder 31 at the rear end and the deadlock slot 30 forms the latching shoulder 32 at the front end.

As shown in FIGS. 13 and 14, the release button 10 is located above the deadlock slot 30 and a locking block 33 is set between the release button 10 and deadlock slot 30. The locking block 33 is slidably connected to tubular body 22 and the sliding direction is parallel to axial direction of tubular body 22. A locking spring 34 is set between locking block 33 and tubular body 22 and the locking spring 34 acts on the sliding direction of locking block 33. A spring tongue 40 is set on the locking block 33 along the axial direction of lancet holder 2 and the spring tongue 40 is an elastic piece and it's located between release button 10 and deadlock slot 30. And the cantilever beam of spring tongue 40 is hanged relatively to locking block 33. 2. The mentioned locking block 33 is set with a sliding block 43 at front end. Under the assembly state, the sliding block 43 at front end of locking block 33 is located in the transition slot 29 and slideably works with transition slot 29. When the front cap 1 is inserted into lancet holder 2 for connection, the pushing face 41 of connecting block 21 contacts the front end of sliding block 43 to push the locking block 33 to move backward.

As shown in FIGS. 15 and 16, a flexible arm 24 extends out from the side of ejection pin 7 and the flexible arm 24 is set with a latch 25 at the cantilever beam end. The latch 25 is set with a bayonet 26 at the front end and a latch hook 27 on the rear end.

The following is the description of present invention according to operation state:

1. State of Installing Lancet

Figure 17:
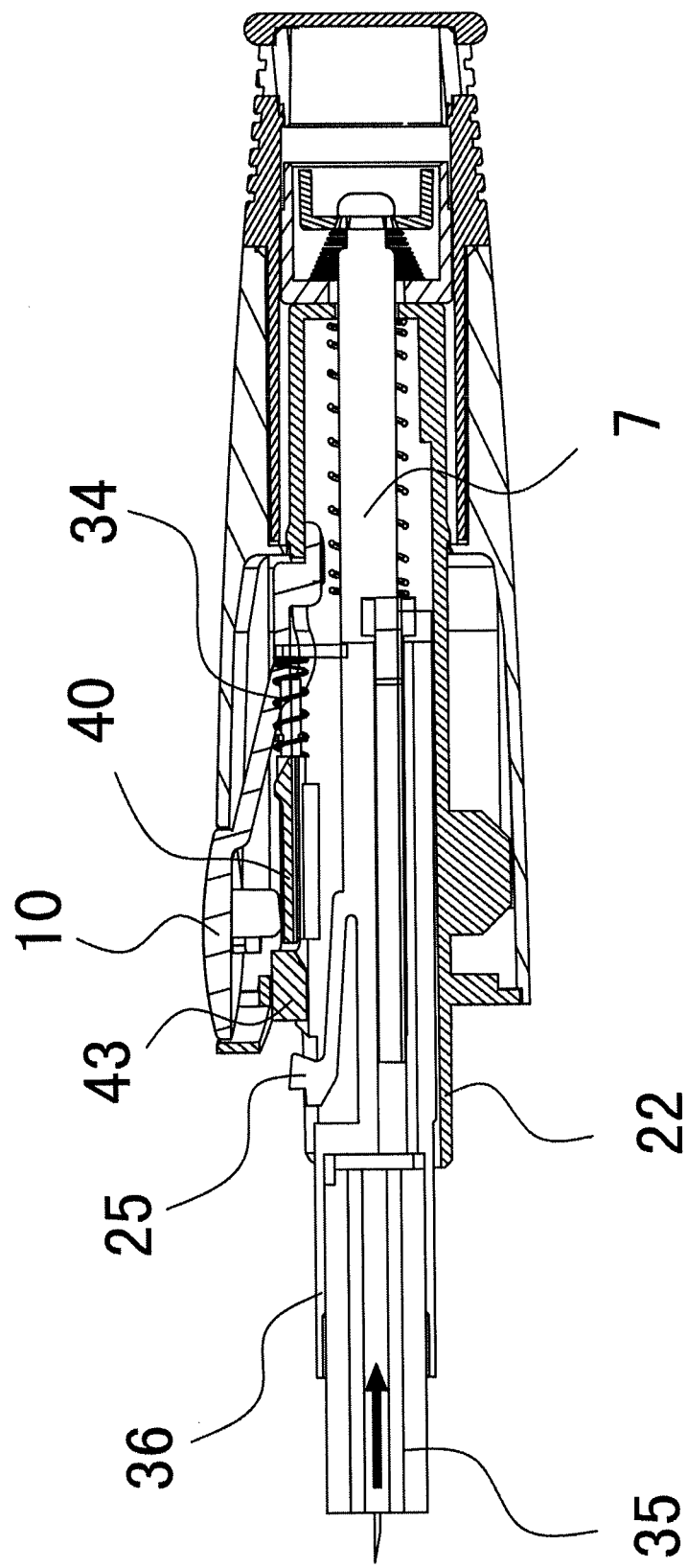
FIG. 17 is a state view of installing lancet on improved safety lancing device of present invention.

As shown in FIG. 17, when the front cap 1 and lancet holder 2 are separated and when the ejecting spring 8 is in free state, the latch 25 is located in slideable slot 28, and when the lancet 35 is inserted into the socket 36 under such state, the inserting forces the latch hook 27 of latch 25 to work with blocking shoulder 31 to prevent the latch 25 from sliding from slideable slot 28 to deadlock slot 30.

Figure 18:
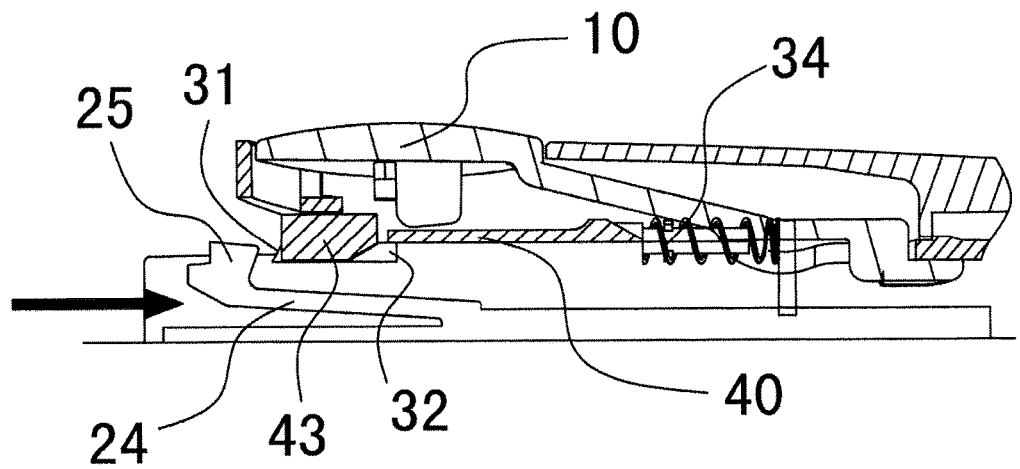
FIG. 18 is a front view of insertion force driving latch to move backward in slideable slot during installation of lancet.
Figure 19:
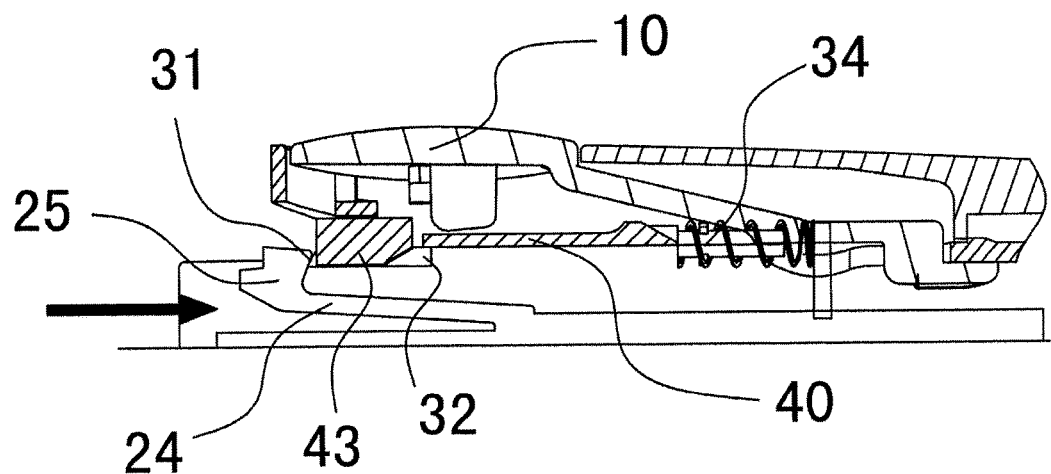
FIG. 19 is a front view of blocking shoulder preventing the latch from moving backward during installation of lancet.

During insertion of lancet 35, the insertion forces the latch 25 to move backward in the the slideable slot 28 shown in FIG. 18. When the latch 25 moves to the rear end of slideable slot 28, the blocking shoulder 31 prevents the latch 25 from continuing to move backward to stop moving backward shown in FIG. 19. When the lancet 35 is installed in position, the latch 25 returns to original position under the action of ejecting spring 8. After the installation of lancet 35, if the front cap is not inserted, the tail handle could not be pulled to enter the locking state before firing due to the blocking of blocking shoulder 31. This is one of important features of present invention to achieve the safe operation.

2. Ready for Firing

Figure 20:
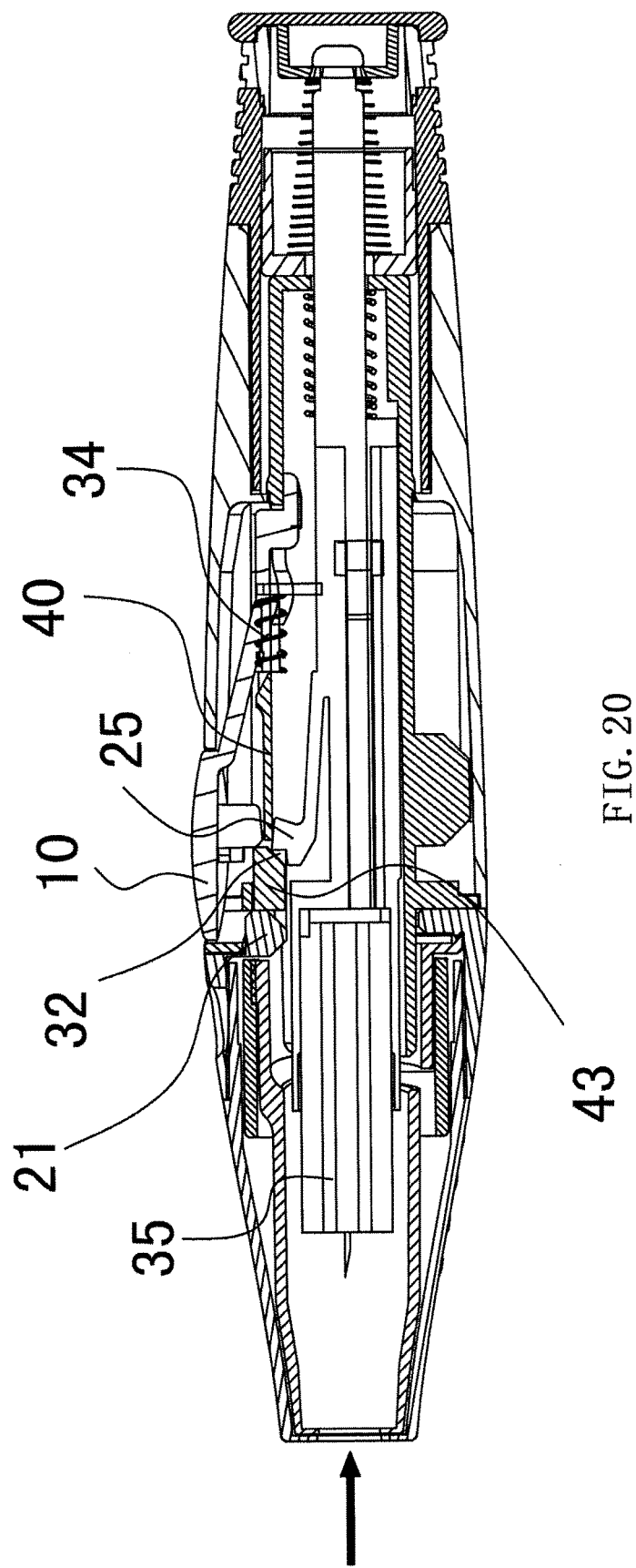
FIG. 20 is a state view of inserted front cap after installing lancet on improved safety lancing device of present invention.
Figure 21:
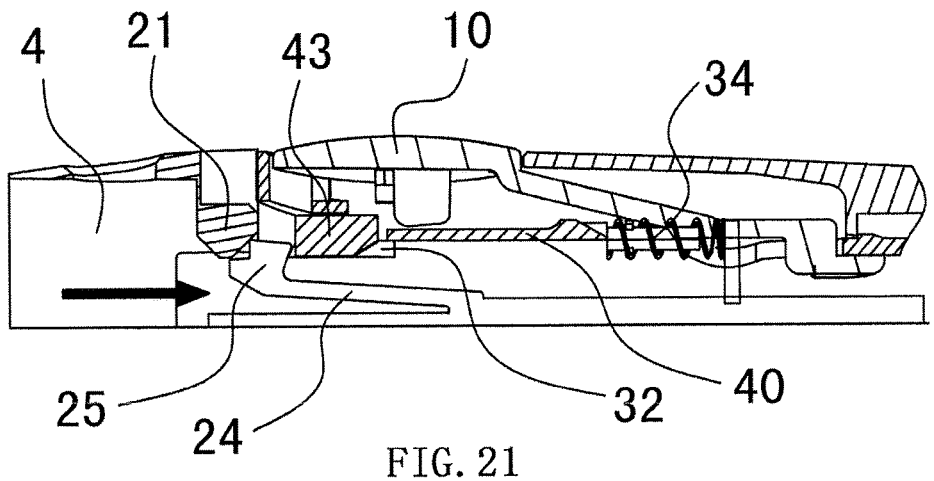
FIG. 21 is a front view of connecting block pushing ejection pin backward through latch during insertion of front cap.
Figure 22:
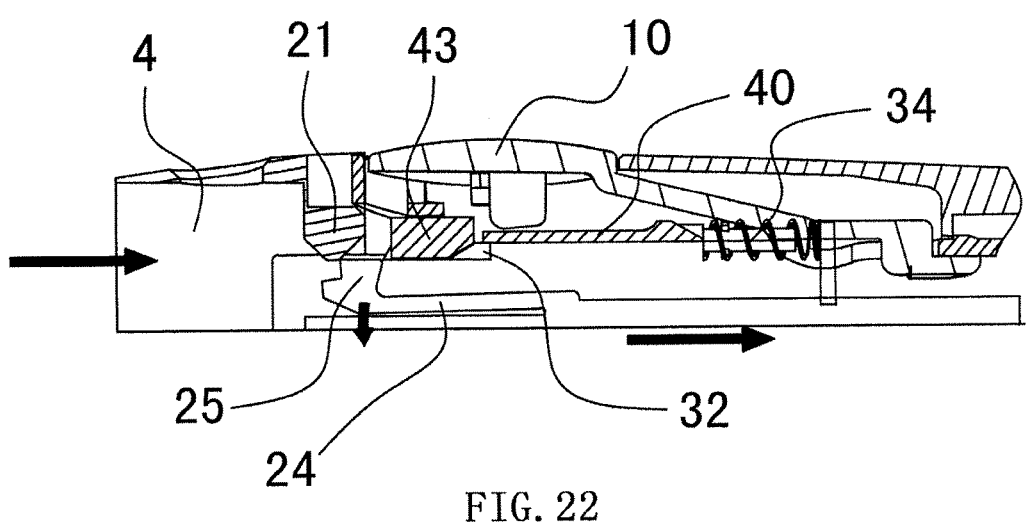
FIG. 22 is a front view of connecting block forcing latch and flexible arm bending to the inner side of front cap during insertion of front cap.
Figure 23:
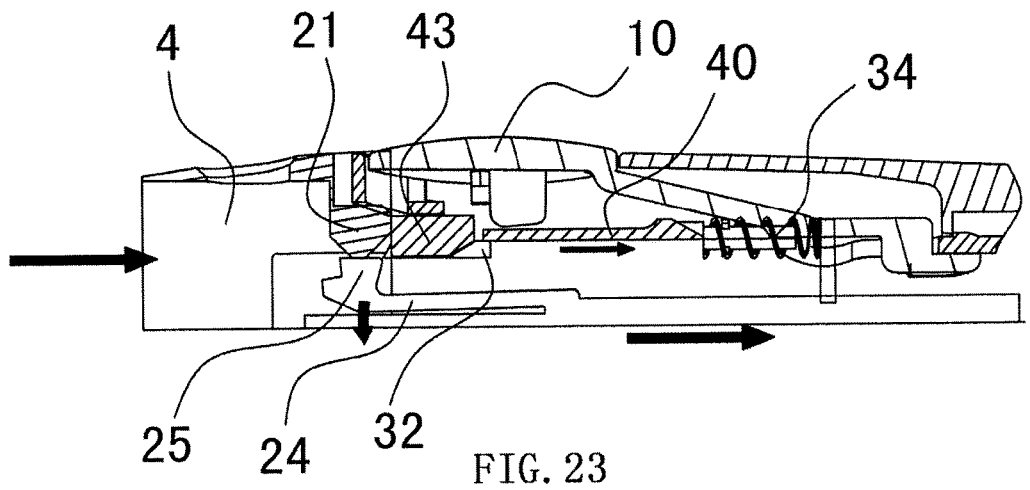
FIG. 23 is a front view of connecting block pushing ejection pin backward through latch during insertion of front cap.
Figure 24:
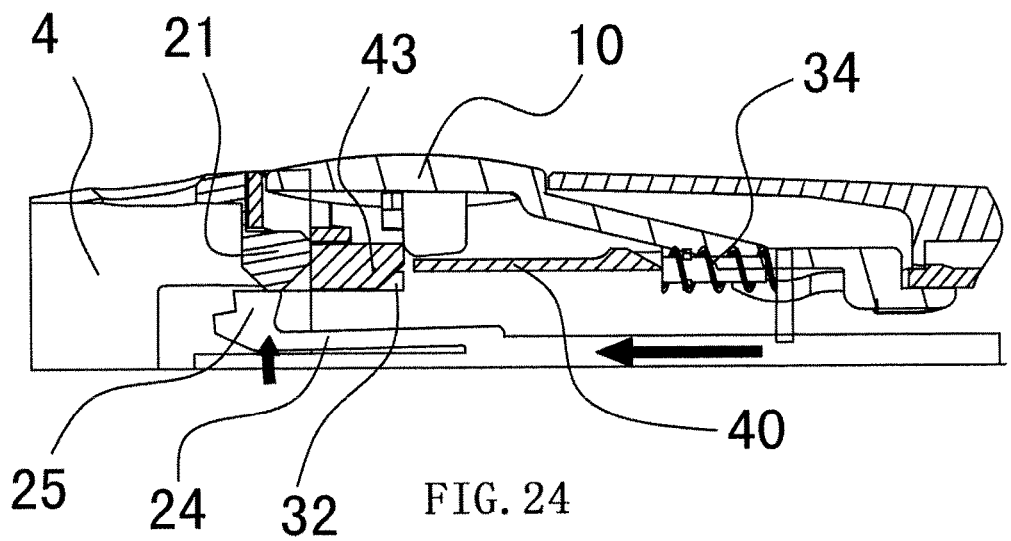
FIG. 24 is a front view of locking block moving backward to release locking spring tongue and ejection pin moving backward during insertion of front cap.

As shown in FIG. 20, when the front cap 1 is inserted into lancet holder 2 for connection, the connecting block 21 is inserted into slideable slot 28. During the insertion process, the convex 42 on the connecting block 21 forces the latch hook 27 of latch 25 to avoid the blocking shoulder 31 by pressing the latch 25 to push the flexible arm 24 to be bent toward the inner side of lancet holder 2 and the pushing face 41 of connecting block 21 pushes the locking block 33 to move backwards driving the front end of spring tongue 40 to avoid the latching shoulder 32 and making release button 10 enter the unlocking state. From FIG. 21~24, it's known that during this process the convex 42 on the connecting block 21 pushes the ejection pin 7 backward; FIG. 42 shows that connecting block 21 forces the latch 25 and flexible arm 24 to be bent toward the inner side of lancet holder 2 and at this time the pushing face 41 on the connecting block 21 doesn't contact the sliding block 43 on the locking block 33; FIG. 23 shows that the pushing face 41 on the connecting block 21 contacts the sliding block 43 and pushes the locking block 33 to move backward; FIG. 24 shows that the locking block 33 moves backward to release the locking spring tongue 40 and the ejection pin moves backward.

Figure 25:
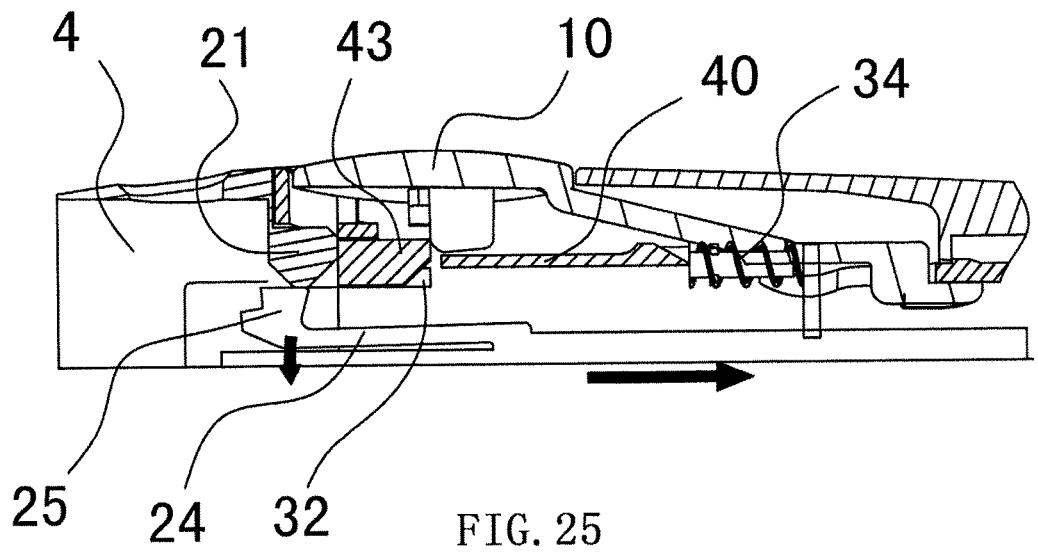
FIG. 25 is a front view of ejection pin driving latch to start to cross transition slot from bottom and move backward through flexible arm during pulling the tail handle backward.
Figure 26:
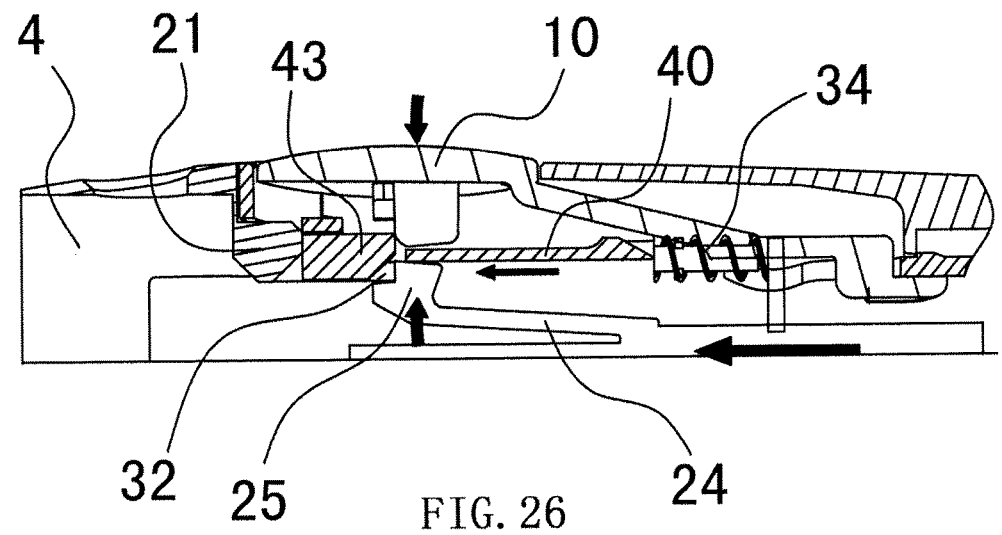
FIG. 26 is a front view of ejection pin driving latch to entirely cross transition slot from bottom to enter deadlock slot through flexible arm and the bayonet at front end of latch locking in the latching shoulder to enter the locking state before firing under the action of ejecting spring and flexible arm.

When the tail handle 16 is pulled backward under such state, the ejection pin 7 drives latch 25 to cross transition slot 29 from bottom to enter deadlock slot 30 through flexible arm 24 and when the tail handle 16 returns to original position, the bayonet 26 at front end of latch 25 locks in the latching shoulder 32 to make ejection pin 32 enter the locking state before firing under the action of ejecting spring 8 and flexible arm 24. It's known from FIG. 25~26 that during this process: FIG. 25 shows ejection pin 7 starting to drive latch 25 to entirely cross transition slot 29 from bottom to move backward through flexible arm 24; FIG. 26 shows latch 25 entirely crossing the transition slot 29 from bottom to enter the deadlock slot 30 and the bayonet 26 at front end of latch 25 locking in the latching shoulder 32 entering the locking state before firing under the action of ejecting spring 8 and flexible arm 24.

3. Firing and Retracting State

Figure 27:
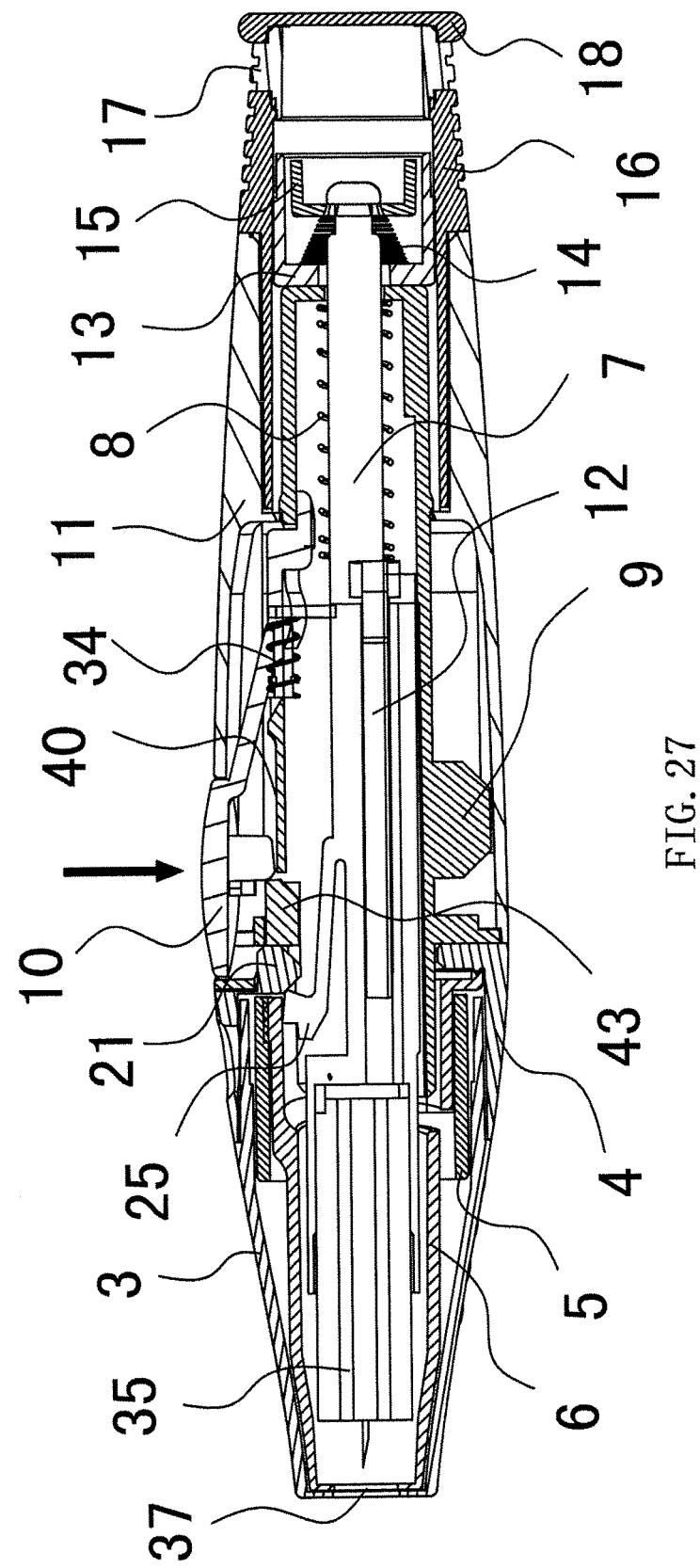
FIG. 27 is a state view of ejection and retraction of improved safety lancing device of present invention.
Figure 28:
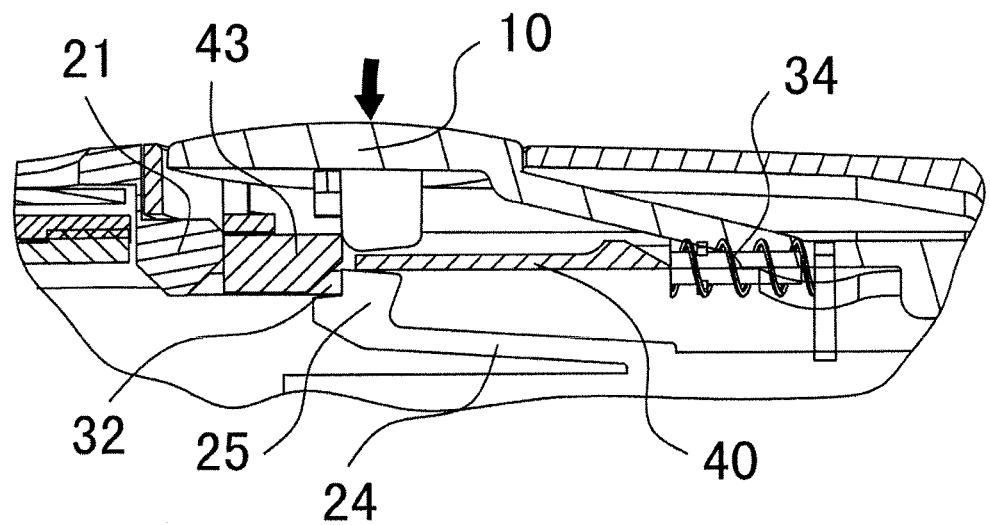
FIG. 28 is an enlarged view of pressing the release button.
Figure 29:
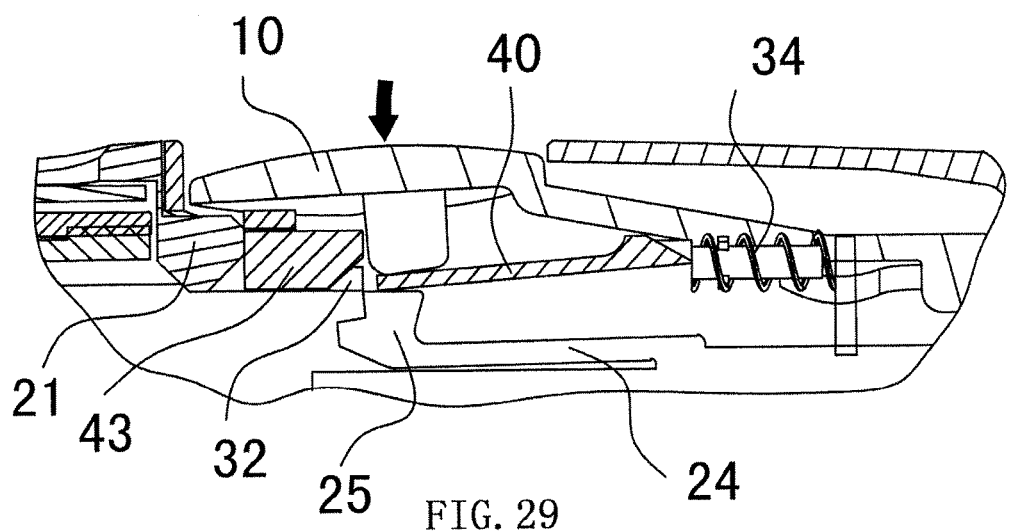
FIG. 29 is an enlarged view of unhooking the latch when pressing the release button.

As shown in FIG. 27, when the release button 10 is pressed, the release button 10 acts on teh latch 25 through the front end of spring tongue 40 to make bayonet 26 move downward along the latching shoulder 32 until it's unhooked to enter the firing state. From this process, it's seen from FIGS. 28 and 29: FIG. 28 shows the state of pressing the release button 10; FIG. 29 shows the state of unhooking of bayonet 26 of latch 25 from latching shoulder 32 when pressing the release button 10. After firing, the ejection pin 7 retracts under the action of reset spring 14 not to expose the needle tip of lancet 35 after firing (shown in FIG. 27).

4. State of Pulling Out Front Cap when Ready for Firing

Figure 30:
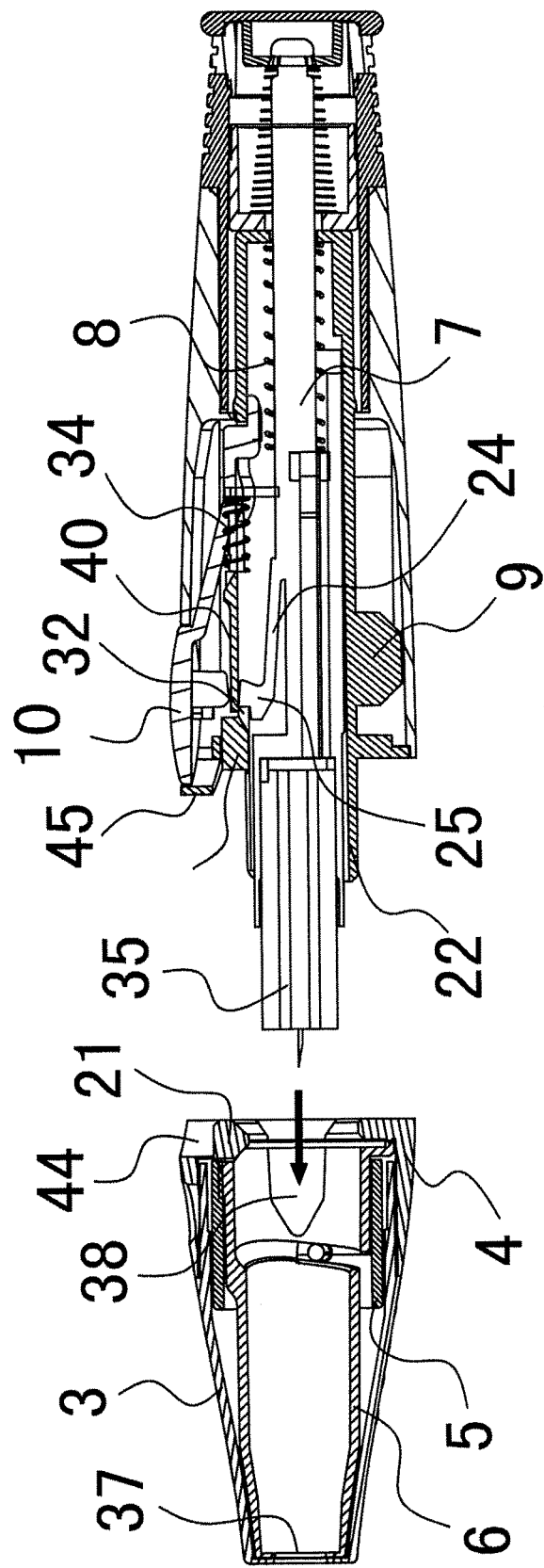
FIG. 30 is a state view of pulling out the front cap under locking state before firing.
Figure 31:
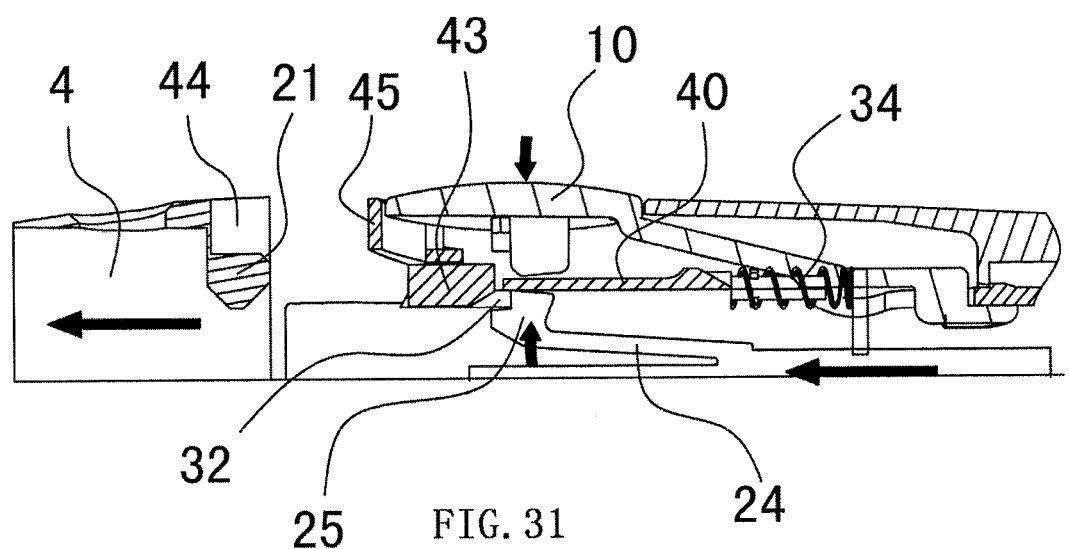
FIG. 31 is a state view of ineffective pressing release button (unable to press) after pulling out the front cap under locking state before firing.

As shown in FIG. 30, under the locking state of ejection pin 7 before firing, when the front cap 1 is pulled out of lancet holder 2, the connecting block 21 is pulled out of slideable slot 28 at the same time, and the locking spring 34 forces the locking block 33 to move forward to the front end and the front end of spring tongue 40 is located up front of latching shoulder 32 to make release button 10 enter locking state. Under such state, the pressing of release button 10 is ineffective. In other words, in the present invention, if the front cap 1 is not inserted, it's impossible for the connecting block 21 to act on the sliding block 43 to push the locking block 33 to move backward, so the release button 10 is always in the locking state (shown in FIGS. 18 and 19, the front end of spring tongue 40 is on the latching shoulder 32). It's known from FIG. 31 that during this process: FIG. 31 shows the ineffective pressing release button (unable to press) after pulling out the front cap 1 under locking state before firing. Now the entire lancing device is in the deadlocking state and this is the second important feature of present invention to achieve the safe operation.

In conclusion, the present invention has two features to achieve the safe operation of lancing device:

Firstly, when the operator inserts the lancet, the insertion force will not make the firing mechanism of lancing device enter the locking state in advance. And when the lancet is not inserted, even pulling the tail handle will not make the firing mechanism of lancing device enter the locking state in advance. In this way, it's possible to prevent the harm to the operator due to misoperation.

Secondly, when the lancing device is ready for firing, if the front cap is not pulled out, it will not trigger the firing mechanism of lancing device. Under this condition, even if the operator presses the release button, it will not trigger the firing mechanism of lancing device. In this way, it's possible to prevent the harm to the operator due to pressing the release button carelessly.

Additionally, as shown in FIG. 2, in order to make the operator recognize the state of firing mechanism in the lancing device easily, the lancet holder 2 is set with a transparent ring 17 at the tail and the ejection pin 7 is set with an indication sleeve 15 (with red mark) at the tail. When the ejection pin 7 is in the locking state before firing, the indication sleeve 15 is located in the transparent ring 17 in axial direction of lancet holder 2. When the operator observes that the transparent ring 17 is with red mark, it denotes that the firing mechanism in the lancing device is in the locking state before firing; when the operator observes that the transparent ring 17 is not with red mark, it denotes that the firing mechanism in the lancing device is in the free state.

About the above-mentioned embodiments, the possible changes of present invention are described as follows:

1. In above-mentioned embodiments, the locking block 33 is set with a spring tongue 40 in axial direction of lancet holder 2 (i.e. the cantilever beam of spring tongue 40 facing forward or backward). It's a possible change if the spring tongue 40 is changed to be transverse, i.e. the cantilever beam of spring tongue 40 facing the side of locking block 33.

2. In above-mentioned embodiments, the locking block 33 is set with a spring tongue 40. It's a possible change if the spring tongue 40 is changed to be a window (not shown in figures). Then the release button 10 acts on the latch 25 through the window. When the window moves away with the locking block 33, the release button 10 could not act on the latch 25 to make release button 10 in locking state.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A kind of improved safety lancing device consists of a front cap and a lancet holder, the front cap is internally equipped with an ejecting cavity in an axial direction, a needle hole is set at a front end of the ejecting cavity and the lancet holder is equipped with an ejection pin and an ejecting spring, the ejection pin is set with a socket to plug a lancet at a head end and the lancet holder is set with a release button at a side and set with a tail handle at a tail end, a rear end of the front cap forms a first connection end and the lancet holder is set with a second connection end corresponding to the first connection end at the front end, and the first connection end and the second connection end are connected in an insert-plug connection wherein:

an inner wall of the ejecting cavity of the first connection end is set with a connecting block, which is set with a pushing face facing the direction of the second connection end and is set with a convex bulge facing the direction of cross section of the ejecting cavity, the shape of the convex bulge is conic, trapezoid or arc on the axial section of the front cap;

the second connection end is set with a section of a tubular body along the axial direction of the lancet holder corresponding to the connecting block and the tubular body is set with a slot on a wall of the tubular body along an axial direction facing the connecting block, and the slot intersects the wall of the tubular body in a radial direction of lancet holder;

a flexible arm extends out from a side of the ejection pin and the flexible arm is set with a latch at a cantilever beam end, the latch is set with a bayonet at the front end and a latch hook on the rear end;

the slot has a section of slideable slot and a section of deadlock slot in the axial direction of lancet holder, the slideable slot is located in front of the deadlock slot, in the radial direction of the lancet holder, the width of the slideable slot and the deadlock slot is larger than that of the latch; the front end of the slideable slot is open ended and the slideable slot is equipped with a blocking shoulder at the rear end and the deadlock slot is equipped with a latching shoulder at the front end; the release button is located above the deadlock slot and a locking block is set between the release button and the deadlock slot, the locking block is slidably connected to the tubular body and the sliding direction is parallel to the axial direction of tubular body, a locking spring is set between the locking block and the tubular body and the locking spring acts on the sliding direction of the locking block, which is set with a spring tongue or a window, the spring tongue is an elastic piece with a cantilever beam and is located between the release button and the deadlock slot, and the cantilever beam of the spring tongue is hanged relatively to the locking block;

when the front cap and the lancet holder are separated, the locking spring forces the locking block to move to the front end of the sliding path and the cantilever beam or window of the spring tongue travels across the latching shoulder to be located above the latching shoulder to make the release button move to a locking state; when the ejecting spring is in a free state, the latch is located in the slideable slot, and when the lancet is inserted into the socket under such state, the inserting forces the latch hook of the latch to work with the blocking shoulder to prevent the latch from sliding from the slideable slot to the deadlock slot;

when the front cap is inserted into the lancet holder for connection, the connecting block is inserted into the slideable slot, during the insertion process, the convex bulge on the connecting block forces the latch hook of the latch to avoid the blocking shoulder by pressing the latch to push the flexible arm to be bent toward the inner side of the lancet holder and the pushing face of the connecting block pushes the locking block to move backwards driving the cantilever beam or window of the spring tongue to avoid the latching shoulder and making the release button enter the unlocking state, under such state, when the tail handle is pulled backward, the ejection pin drives the latch to travel across the slideable slot to enter the deadlock slot through the flexible arm, and when the tail handle returns to an original position, the bayonet at the front end of the latch is locked in the latching shoulder to make the ejection pin enter the locking state before firing under an elastic force of the ejecting spring and the flexible arm; when the release button is pressed, the release button acts on the latch through the cantilever beam or window of the spring tongue to make the bayonet slide downward along the latching shoulder until it is unhooked to enter a firing state;

under the locking state of the ejection pin before firing, when the front cap is pulled out of the lancet holder, the connecting block is pulled out of the slideable slot at the same time, and the locking spring forces the locking block to move forward to the front end and the cantilever beam or window of the spring tongue travels across the latching shoulder to be located up front of the latching shoulder to make the release button enter the locking state, under such state, the pressing of the release button is ineffective;

wherein the axial direction is the direction between a tip and a tail of the lancing device and the radial direction is a horizontal direction of the lancing device.

2. An improved safety lancing device according to claim 1 wherein the locking block is set with a sliding block at a front end, when the front cap is inserted into the lancet holder for connection, the pushing face of the connecting block contacts the front end of the sliding block to push the locking block to move backward.

3. An improved safety lancing device according to claim 2 wherein a section of transition slot is set between the slideable slot and the deadlock slot to make the slot comprise a section of slideable slot, a section of transition slot and a section of deadlock slot in the axial direction of the lancet holder, the width of the transition slot is less than the width of the latch under the loading state, the sliding block at the front end of the locking block is in the transition slot and slides along the transition slot.

4. An improved safety lancing device according to claim 1 wherein a hollow guiding slot is set on the inner wall of the ejecting cavity of the first connection end of the front cap and a raised guiding track is set on the outer wall of the tubular body of the second connection end of the lancet holder corresponding to the guiding slot, when the front cap is inserted into the lancet holder for connection, the guiding track and guiding slot are connected.

5. An improved safety lancing device according to claim 4 wherein on a matching surface of the insert-plug connection of the first connection end and the second connection end, one side is set with a recess and another side is set with a convex surface, when the front cap is inserted into the lancet holder for connection, the recess and the convex surface match together.

6. An improved safety lancing device according to claim 1 wherein the tail of the lancet holder is equipped with a transparent ring and the tail of the ejection pin is equipped with an indication sleeve, when the ejection pin is in the locking state before firing, the indication sleeve is located in the transparent ring of the lancet holder in the axial direction.

* * * * *